US012508032B2

(12) United States Patent
Gorochow et al.

(10) Patent No.: US 12,508,032 B2
(45) Date of Patent: Dec. 30, 2025

(54) MEDICAL DEVICE DELIVERY SYSTEMS WITH TWISTING LOOP WIRES

(71) Applicant: DePuy Synthes Products, Inc., Raynham, MA (US)

(72) Inventors: Lacey Gorochow, Raynham, MA (US); Robert Slazas, Raynham, MA (US); Zhixian Chen, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/566,907

(22) Filed: Dec. 31, 2021

(65) Prior Publication Data

US 2023/0210535 A1 Jul. 6, 2023

(51) Int. Cl.
*A61B 17/12* (2006.01)

(52) U.S. Cl.
CPC .... *A61B 17/1214* (2013.01); *A61B 17/12113* (2013.01); *A61B 2017/12054* (2013.01)

(58) Field of Classification Search
CPC .... A61B 2017/12054; A61B 17/12113; A61B 17/1214; A61B 17/12054; A61B 17/12022; A61B 17/1205; A61B 17/12027; A61B 17/12031; A61B 17/12036; A61B 17/1204; A61B 17/12045; A61B 17/12122; A61B 17/12109; A61B 17/12104; A61B 17/12099; A61B 17/12136; A61B 2017/1205; A61F 2/95; A61F 2/954; A61F 2/00; A61F 2/01; A61F 2/011; A61F 2002/9505; A61F 2002/9511; A61F 2002/9528; A61F 2002/9534
See application file for complete search history.

(56) References Cited

U.S. PATENT DOCUMENTS

| | | | |
|---|---|---|---|
| 2,220,203 | A | 11/1940 | Branin |
| 3,429,408 | A | 2/1969 | Maker et al. |
| 4,858,810 | A | 8/1989 | Intlekofer et al. |
| 5,069,674 | A | 12/1991 | Fearnot et al. |
| 5,108,407 | A | 4/1992 | Geremia et al. |
| 5,122,136 | A | 6/1992 | Guglielmi et al. |
| D329,698 | S | 9/1992 | Loney et al. |
| 5,234,437 | A | 8/1993 | Sepetka |
| 5,250,071 | A | 10/1993 | Palermo |
| 5,263,964 | A | 11/1993 | Purdy |

(Continued)

FOREIGN PATENT DOCUMENTS

| | | | |
|---|---|---|---|
| CN | 102125451 | A | 7/2011 |
| CN | 103356260 | A | 10/2013 |

(Continued)

OTHER PUBLICATIONS

Extended European Search Report issued in corresponding EP Application No. 22 21 7254 dated Mar. 17, 2023.

*Primary Examiner* — Majid Jamialahmadi

(74) *Attorney, Agent, or Firm* — Troutman Pepper Locke LLP

(57) ABSTRACT

A detachment system for delivering an embolic coil implant to a treatment site is provided. A loop wire that is looped over a pull wire of the system can include one or more twists to increase frictional resistance against the pull wire. The additional resistance decreases likelihood of premature deployment of the embolic coil prior to the detachment system reaching the treatment site.

19 Claims, 7 Drawing Sheets

(56) References Cited

U.S. PATENT DOCUMENTS

| | | | |
|---|---|---|---|
| 5,334,210 | A | 8/1994 | Gianturco |
| 5,350,397 | A | 9/1994 | Palermo et al. |
| 5,382,259 | A | 1/1995 | Phelps et al. |
| 5,392,791 | A | 2/1995 | Nyman |
| 5,484,409 | A | 1/1996 | Atkinson et al. |
| 5,536,248 | A | 7/1996 | Weaver et al. |
| 5,569,221 | A | 10/1996 | Houser et al. |
| 5,645,558 | A | 7/1997 | Horton |
| 5,899,935 | A | 5/1999 | Ding |
| 5,925,059 | A | 7/1999 | Palermo et al. |
| 6,113,622 | A | 9/2000 | Hieshima |
| 6,203,547 | B1 | 3/2001 | Nguyen et al. |
| 6,391,037 | B1 | 5/2002 | Greenhalgh |
| 6,454,780 | B1 | 9/2002 | Wallace |
| 6,506,204 | B2 | 1/2003 | Mazzocchi |
| 6,561,988 | B1 | 5/2003 | Turturro et al. |
| 7,367,987 | B2 | 5/2008 | Balgobin et al. |
| 7,371,251 | B2 | 5/2008 | Mitelberg et al. |
| 7,371,252 | B2 | 5/2008 | Balgobin et al. |
| 7,377,932 | B2 | 5/2008 | Mitelberg et al. |
| 7,384,407 | B2 | 6/2008 | Rodriguez et al. |
| 7,708,754 | B2 | 5/2010 | Balgobin et al. |
| 7,708,755 | B2 | 5/2010 | Davis, III et al. |
| 7,799,052 | B2 | 9/2010 | Balgobin et al. |
| 7,811,305 | B2 | 10/2010 | Balgobin et al. |
| 7,819,891 | B2 | 10/2010 | Balgobin et al. |
| 7,819,892 | B2 | 10/2010 | Balgobin et al. |
| 7,901,444 | B2 | 3/2011 | Slazas |
| 7,985,238 | B2 | 7/2011 | Balgobin et al. |
| 8,062,325 | B2 | 11/2011 | Mitelberg et al. |
| 8,333,796 | B2 | 12/2012 | Tompkins et al. |
| 8,926,650 | B2 | 1/2015 | Que et al. |
| 8,956,381 | B2 | 2/2015 | Que et al. |
| 9,155,540 | B2 | 10/2015 | Lorenzo |
| 9,232,992 | B2 | 1/2016 | Heidner |
| 9,314,326 | B2 | 4/2016 | Wallace et al. |
| 9,532,792 | B2 | 1/2017 | Galdonik et al. |
| 9,532,873 | B2 | 1/2017 | Kelley |
| 9,533,344 | B2 | 1/2017 | Monetti et al. |
| 9,539,011 | B2 | 1/2017 | Chen et al. |
| 9,539,022 | B2 | 1/2017 | Bowman |
| 9,539,122 | B2 | 1/2017 | Burke et al. |
| 9,539,382 | B2 | 1/2017 | Nelson |
| 9,549,830 | B2 | 1/2017 | Bruszewski et al. |
| 9,554,805 | B2 | 1/2017 | Tompkins et al. |
| 9,561,125 | B2 | 2/2017 | Bowman et al. |
| 9,572,982 | B2 | 2/2017 | Burnes et al. |
| 9,579,484 | B2 | 2/2017 | Barnell |
| 9,585,642 | B2 | 3/2017 | Dinsmoor et al. |
| 9,615,832 | B2 | 4/2017 | Bose et al. |
| 9,615,951 | B2 | 4/2017 | Bennett et al. |
| 9,622,753 | B2 | 4/2017 | Cox |
| 9,636,115 | B2 | 5/2017 | Henry et al. |
| 9,636,439 | B2 | 5/2017 | Chu et al. |
| 9,642,675 | B2 | 5/2017 | Werneth et al. |
| 9,655,633 | B2 | 5/2017 | Leynov et al. |
| 9,655,645 | B2 | 5/2017 | Staunton |
| 9,655,989 | B2 | 5/2017 | Cruise et al. |
| 9,662,120 | B2 | 5/2017 | Lagodzki et al. |
| 9,662,129 | B2 | 5/2017 | Galdonik et al. |
| 9,662,238 | B2 | 5/2017 | Dwork et al. |
| 9,662,425 | B2 | 5/2017 | Lilja et al. |
| 9,668,898 | B2 | 6/2017 | Wong |
| 9,675,477 | B2 | 6/2017 | Thompson |
| 9,675,782 | B2 | 6/2017 | Connolly |
| 9,676,022 | B2 | 6/2017 | Ensign et al. |
| 9,692,557 | B2 | 6/2017 | Murphy |
| 9,693,852 | B2 | 7/2017 | Lam et al. |
| 9,700,262 | B2 | 7/2017 | Janik et al. |
| 9,700,399 | B2 | 7/2017 | Acosta-Acevedo |
| 9,717,421 | B2 | 8/2017 | Griswold et al. |
| 9,717,500 | B2 * | 8/2017 | Tieu ................. A61B 17/12113 |
| 9,717,502 | B2 | 8/2017 | Teoh et al. |
| 9,724,103 | B2 | 8/2017 | Cruise et al. |
| 9,724,526 | B2 | 8/2017 | Strother et al. |
| 9,750,565 | B2 | 9/2017 | Bloom et al. |
| 9,757,260 | B2 | 9/2017 | Greenan |
| 9,764,111 | B2 | 9/2017 | Gulachenski |
| 9,770,251 | B2 | 9/2017 | Bowman et al. |
| 9,770,577 | B2 | 9/2017 | Li et al. |
| 9,775,621 | B2 | 10/2017 | Tompkins et al. |
| 9,775,706 | B2 | 10/2017 | Paterson et al. |
| 9,775,732 | B2 | 10/2017 | Khenansho |
| 9,788,800 | B2 | 10/2017 | Mayoras, Jr. |
| 9,795,391 | B2 | 10/2017 | Saatchi et al. |
| 9,801,980 | B2 | 10/2017 | Karino et al. |
| 9,808,599 | B2 | 11/2017 | Bowman et al. |
| 9,833,252 | B2 | 12/2017 | Sepetka et al. |
| 9,833,604 | B2 | 12/2017 | Lam et al. |
| 9,833,625 | B2 | 12/2017 | Waldhauser et al. |
| 9,918,718 | B2 | 3/2018 | Lorenzo |
| 10,149,676 | B2 | 12/2018 | Mirigian et al. |
| 10,285,710 | B2 | 5/2019 | Lorenzo et al. |
| 10,292,851 | B2 | 5/2019 | Gorochow |
| 10,420,563 | B2 | 9/2019 | Hebert et al. |
| 10,517,604 | B2 | 12/2019 | Bowman et al. |
| 10,668,258 | B1 | 6/2020 | Calhoun et al. |
| 10,806,402 | B2 | 10/2020 | Cadieu et al. |
| 10,806,461 | B2 | 10/2020 | Lorenzo |
| 11,951,026 | B2 | 4/2024 | Clinger et al. |
| 2001/0049519 | A1 | 12/2001 | Holman et al. |
| 2002/0072705 | A1 | 6/2002 | Vrba et al. |
| 2002/0165569 | A1 | 11/2002 | Ramzipoor et al. |
| 2002/0183786 | A1 | 12/2002 | Girton |
| 2003/0009208 | A1 | 1/2003 | Snyder et al. |
| 2003/0093094 | A1 | 5/2003 | Diaz et al. |
| 2003/0181942 | A1 | 9/2003 | Sutton et al. |
| 2004/0034363 | A1 | 2/2004 | Wilson et al. |
| 2004/0059367 | A1 | 3/2004 | Davis et al. |
| 2004/0087964 | A1 | 5/2004 | Diaz et al. |
| 2006/0025801 | A1 | 2/2006 | Lulo et al. |
| 2006/0064151 | A1 | 3/2006 | Guterman |
| 2006/0100687 | A1 | 5/2006 | Fahey et al. |
| 2006/0116711 | A1 | 6/2006 | Elliott et al. |
| 2006/0116714 | A1 | 6/2006 | Sepetka et al. |
| 2006/0135986 | A1 | 6/2006 | Wallace et al. |
| 2006/0206139 | A1 | 9/2006 | Tekulve |
| 2006/0241685 | A1 | 10/2006 | Wilson et al. |
| 2006/0247677 | A1 | 11/2006 | Cheng et al. |
| 2006/0276824 | A1 | 12/2006 | Mitelberg et al. |
| 2006/0276825 | A1 | 12/2006 | Mitelberg et al. |
| 2006/0276826 | A1 | 12/2006 | Mitelberg et al. |
| 2006/0276827 | A1 | 12/2006 | Mitelberg et al. |
| 2006/0276830 | A1 | 12/2006 | Balgobin et al. |
| 2006/0276833 | A1 | 12/2006 | Balgobin et al. |
| 2007/0010850 | A1 | 1/2007 | Balgobin et al. |
| 2007/0055302 | A1 | 3/2007 | Henry et al. |
| 2007/0083132 | A1 | 4/2007 | Sharrow |
| 2007/0203519 | A1 | 8/2007 | Lorenzo et al. |
| 2007/0233168 | A1 | 10/2007 | Davis et al. |
| 2007/0270903 | A1 | 11/2007 | Davis, III et al. |
| 2008/0027561 | A1 | 1/2008 | Mitelberg et al. |
| 2008/0045997 | A1 | 2/2008 | Balgobin et al. |
| 2008/0097462 | A1 | 4/2008 | Mitelberg et al. |
| 2008/0119887 | A1 | 5/2008 | Que et al. |
| 2008/0269719 | A1 | 10/2008 | Balgobin et al. |
| 2008/0269721 | A1 | 10/2008 | Balgobin et al. |
| 2008/0281350 | A1 | 11/2008 | Sepetka |
| 2008/0300616 | A1 | 12/2008 | Que et al. |
| 2008/0306503 | A1 | 12/2008 | Que et al. |
| 2009/0062726 | A1 | 3/2009 | Ford et al. |
| 2009/0099592 | A1 | 4/2009 | Buiser et al. |
| 2009/0270877 | A1 | 10/2009 | Johnson et al. |
| 2009/0312748 | A1 | 12/2009 | Johnson et al. |
| 2010/0094395 | A1 | 4/2010 | Kellett |
| 2010/0114017 | A1 | 5/2010 | Lenker et al. |
| 2010/0206453 | A1 | 8/2010 | Leeflang et al. |
| 2010/0324649 | A1 | 12/2010 | Mattsson |
| 2011/0092997 | A1 | 4/2011 | Kang |
| 2011/0118772 | A1 | 5/2011 | Chen et al. |
| 2011/0118776 | A1 | 5/2011 | Chen et al. |
| 2011/0202085 | A1 | 8/2011 | Loganathan et al. |
| 2011/0295303 | A1 | 12/2011 | Freudenthal |
| 2012/0035707 | A1 | 2/2012 | Mitelberg et al. |

(56) References Cited

U.S. PATENT DOCUMENTS

2012/0041472 A1 2/2012 Tan et al.
2012/0083868 A1 4/2012 Shrivastava et al.
2012/0172913 A1* 7/2012 Kurrus ............ A61B 17/12022 606/200
2012/0172921 A1 7/2012 Yamanaka et al.
2012/0179194 A1 7/2012 Wilson et al.
2012/0283768 A1 11/2012 Cox et al.
2012/0289772 A1 11/2012 O'Connell et al.
2013/0066413 A1 3/2013 Jin et al.
2013/0296915 A1 11/2013 Bodewadt
2013/0325054 A1 12/2013 Watson
2013/0338678 A1 12/2013 Loushin et al.
2014/0058435 A1 2/2014 Jones et al.
2014/0088565 A1 3/2014 Vongphakdy et al.
2014/0135812 A1 5/2014 Divino et al.
2014/0200607 A1 7/2014 Sepetka et al.
2014/0207175 A1 7/2014 Aggerholm
2014/0243883 A1 8/2014 Tsukashima et al.
2014/0277078 A1 9/2014 Slazas et al.
2014/0277084 A1 9/2014 Mirigian et al.
2014/0277085 A1 9/2014 Mirigian et al.
2014/0277092 A1 9/2014 Teoh et al.
2014/0277093 A1 9/2014 Guo et al.
2014/0277100 A1 9/2014 Kang
2015/0005808 A1 1/2015 Chouinard et al.
2015/0025562 A1 1/2015 Dinh et al.
2015/0119884 A1 4/2015 Fung et al.
2015/0164666 A1 6/2015 Johnson et al.
2015/0182227 A1 7/2015 Le et al.
2015/0230802 A1 8/2015 Lagodzki et al.
2015/0335333 A1 11/2015 Jones et al.
2016/0008003 A1 1/2016 Kleshinski et al.
2016/0022275 A1 1/2016 Garza
2016/0022445 A1 1/2016 Ruvalacaba et al.
2016/0045347 A1 2/2016 Smouse et al.
2016/0157869 A1 6/2016 Elgård et al.
2016/0228125 A1 8/2016 Pederson, Jr. et al.
2016/0278782 A1 9/2016 Anderson et al.
2016/0310304 A1 10/2016 Mialhe
2016/0331383 A1 11/2016 Hebert et al.
2016/0346508 A1 12/2016 Williams et al.
2017/0007264 A1 1/2017 Cruise et al.
2017/0007265 A1 1/2017 Guo et al.
2017/0020670 A1 1/2017 Murray et al.
2017/0020700 A1 1/2017 Bienvenu et al.
2017/0027640 A1 2/2017 Kunis et al.
2017/0027692 A1 2/2017 Bonhoeffer et al.
2017/0027725 A1 2/2017 Argentine
2017/0035436 A1 2/2017 Morita
2017/0035567 A1 2/2017 Duffy
2017/0042548 A1 2/2017 Lam
2017/0049596 A1 2/2017 Schabert
2017/0071737 A1 3/2017 Kelley
2017/0072165 A1 3/2017 Lim et al.
2017/0072452 A1 3/2017 Monetti et al.
2017/0079671 A1 3/2017 Morero et al.
2017/0079680 A1 3/2017 Bowman
2017/0079766 A1 3/2017 Wang et al.
2017/0079767 A1 3/2017 Leon-Yip
2017/0079812 A1 3/2017 Lam et al.
2017/0079817 A1 3/2017 Sepetka et al.
2017/0079819 A1 3/2017 Pung et al.
2017/0079820 A1 3/2017 Lam et al.
2017/0086851 A1 3/2017 Wallace et al.
2017/0086996 A1 3/2017 Peterson et al.
2017/0095258 A1 4/2017 Tassoni et al.
2017/0095259 A1 4/2017 Tompkins et al.
2017/0100126 A1 4/2017 Bowman et al.
2017/0100141 A1 4/2017 Morero et al.
2017/0100143 A1 4/2017 Granfield
2017/0100183 A1 4/2017 Iaizzo et al.
2017/0105739 A1 4/2017 Dias et al.
2017/0113023 A1 4/2017 Steingisser et al.
2017/0147765 A1 5/2017 Mehta
2017/0151032 A1 6/2017 Loisel
2017/0165062 A1 6/2017 Rothstein
2017/0165065 A1 6/2017 Rothstein et al.
2017/0165454 A1 6/2017 Tuohy et al.
2017/0172581 A1 6/2017 Bose et al.
2017/0172766 A1 6/2017 Vong et al.
2017/0172772 A1 6/2017 Khenansho
2017/0189033 A1 7/2017 Sepetka et al.
2017/0189035 A1 7/2017 Porter
2017/0215902 A1 8/2017 Leynov et al.
2017/0216484 A1 8/2017 Cruise et al.
2017/0224350 A1 8/2017 Shimizu et al.
2017/0224355 A1 8/2017 Bowman et al.
2017/0224467 A1 8/2017 Piccagli et al.
2017/0224511 A1 8/2017 Dwork et al.
2017/0224953 A1 8/2017 Tran et al.
2017/0231749 A1 8/2017 Perkins et al.
2017/0245864 A1 8/2017 Franano et al.
2017/0245885 A1 8/2017 Lenker
2017/0252064 A1 9/2017 Staunton
2017/0258476 A1 9/2017 Hayakawa et al.
2017/0265983 A1 9/2017 Lam et al.
2017/0281192 A1 10/2017 Tieu et al.
2017/0281331 A1 10/2017 Perkins et al.
2017/0281344 A1 10/2017 Costello
2017/0281909 A1 10/2017 Northrop et al.
2017/0281912 A1 10/2017 Melder et al.
2017/0290593 A1 10/2017 Cruise et al.
2017/0290654 A1 10/2017 Sethna
2017/0296324 A1 10/2017 Argentine
2017/0296325 A1 10/2017 Marrocco et al.
2017/0303939 A1 10/2017 Greenhalgh et al.
2017/0303942 A1 10/2017 Greenhalgh et al.
2017/0303947 A1 10/2017 Greenhalgh et al.
2017/0303948 A1 10/2017 Wallace et al.
2017/0304041 A1 10/2017 Argentine
2017/0304097 A1 10/2017 Corwin et al.
2017/0304595 A1 10/2017 Nagasrinivasa et al.
2017/0312109 A1 11/2017 Le
2017/0312484 A1 11/2017 Shipley et al.
2017/0316561 A1 11/2017 Helm et al.
2017/0319826 A1 11/2017 Bowman et al.
2017/0333228 A1 11/2017 Orth et al.
2017/0333236 A1 11/2017 Greenan
2017/0333678 A1 11/2017 Bowman et al.
2017/0340383 A1 11/2017 Bloom et al.
2017/0348014 A1 12/2017 Wallace et al.
2017/0348514 A1 12/2017 Guyon et al.
2017/0367712 A1 12/2017 Johnson et al.
2018/0028779 A1 2/2018 von Oepen et al.
2018/0036508 A1 2/2018 Ozasa et al.
2018/0078263 A1 3/2018 Stoppenhagen et al.
2018/0228493 A1 8/2018 Aguilar et al.
2018/0250150 A1 9/2018 Majercak et al.
2018/0280667 A1 10/2018 Keren
2018/0289375 A1 10/2018 Hebert et al.
2018/0296222 A1 10/2018 Hebert et al.
2018/0325706 A1 11/2018 Hebert et al.
2019/0142565 A1 5/2019 Follmer et al.
2019/0159784 A1 5/2019 Sananes et al.
2019/0192162 A1 6/2019 Lorenzo et al.
2019/0201688 A1 7/2019 Olson
2019/0231566 A1 8/2019 Tassoni et al.
2019/0255290 A1 8/2019 Snyder et al.
2019/0314033 A1 10/2019 Mirigian et al.
2019/0328398 A1 10/2019 Lorenzo
2020/0015876 A1 1/2020 Chou et al.
2020/0078024 A1 3/2020 Tekulve
2020/0138448 A1 5/2020 Dasnurkar et al.
2020/0147347 A1 5/2020 Cottone
2020/0187951 A1 6/2020 Blumenstyk
2020/0229957 A1 7/2020 Bardsley et al.
2020/0397444 A1 12/2020 Montidoro et al.
2020/0406048 A1 12/2020 Rentas Torres et al.
2021/0001082 A1 1/2021 Lorenzo et al.
2021/0045759 A1 2/2021 Merhi et al.
2021/0085498 A1 3/2021 Nygaard et al.
2021/0100555 A1* 4/2021 Lorenzo ............ A61M 25/0662
2021/0186513 A1* 6/2021 Hoshino ............ A61B 17/1214
2021/0196281 A1 7/2021 Blumenstyk et al.

(56) References Cited

U.S. PATENT DOCUMENTS

| | | | | |
|---|---|---|---|---|
| 2021/0213252 | A1 | 7/2021 | Lorenzo et al. | |
| 2021/0220013 | A1 | 7/2021 | Libarnes et al. | |
| 2021/0338248 | A1 | 11/2021 | Lorenzo et al. | |
| 2021/0346002 | A1 * | 11/2021 | Lorenzo | A61M 25/09 |
| 2021/0353299 | A1 | 11/2021 | Hamel et al. | |

FOREIGN PATENT DOCUMENTS

| | | | | |
|---|---|---|---|---|
| CN | 104203341 | A | 12/2014 | |
| CN | 106456422 | A | 2/2017 | |
| CN | 109770985 | A | 5/2019 | |
| EP | 1985244 | A2 | 10/2008 | |
| EP | 2498691 | | 9/2012 | |
| EP | 3092956 | A1 | 11/2016 | |
| EP | 3501427 | A1 | 6/2019 | |
| EP | 3795097 | A1 | 3/2021 | |
| EP | 3799803 | A1 | 4/2021 | |
| EP | 3854321 | A1 | 7/2021 | |
| EP | 1188414 | A1 | 3/2022 | |
| EP | 4119065 | A1 | 1/2023 | |
| JP | H10-507090 | A | 7/1998 | |
| JP | 2006-334408 | A | 12/2006 | |
| JP | 2006346350 | A | 12/2006 | |
| JP | 2012-523943 | A | 10/2012 | |
| JP | 2013-78584 | A | 5/2013 | |
| JP | 2014-399 | A | 1/2014 | |
| JP | 2016-179174 | A | 10/2016 | |
| JP | 2017-529894 | A | 10/2017 | |
| WO | WO 2007/070793 | A2 | 6/2007 | |
| WO | WO-2008064209 | A1 * | 5/2008 | A61B 17/12022 |
| WO | WO 2009/132045 | A2 | 10/2009 | |
| WO | WO 2012/158152 | A1 | 11/2012 | |
| WO | WO 2016/014985 | A1 | 1/2016 | |
| WO | WO 2017/066386 | A1 | 4/2017 | |
| WO | WO 2018/022186 | A1 | 2/2018 | |
| WO | WO 2020/148768 | A1 | 7/2020 | |

* cited by examiner

MEDICAL DEVICE DELIVERY SYSTEMS WITH TWISTING LOOP WIRES

FIELD OF INVENTION

This invention generally relates to intravascular medical device systems that navigate through body vessels of a human subject and, more particularly, to detachment/delivery systems for delivering and deploying an implantable medical device to a target location of a body vessel and methods of using the same.

BACKGROUND

Aneurysms can be intravascularly treated by delivering a treatment device to the aneurysm to fill the sac of the aneurysm with embolic material and/or block the neck of the aneurysm to inhibit blood flow into the aneurysm. When filling the aneurysm sac, the embolic material can promote blood clotting to create a thrombotic mass within the aneurysm. When treating the aneurysm neck without substantially filling the aneurysm sac, blood flow into the neck of the aneurysm can be inhibited to induce venous stasis in the aneurysm and facilitate natural formation of a thrombotic mass within the aneurysm.

In some current treatments, multiple embolic coils are used to either fill the aneurysm sac or treat the entrance of the aneurysm neck. A common challenge among embolic coil treatments is that implanted coils and implanted portions of partially implanted coils can become entangled and difficult to reposition. In some instances, a physician may not be able to retract a partially implanted coil and may be forced to position the coil in a non-ideal location. Improperly positioning embolic coils at the aneurysm neck can potentially have the adverse effect of impeding the flow of blood in the adjoining blood vessel, particularly if the entrance and/or sac is overpacked. If a portion of the improperly placed coil becomes dislodged, it can enter the neighboring blood vessel and promote clot formation, which can ultimately lead to an obstruction that is tethered to the aneurysm and therefor extremely difficult to treat. Conversely, if the entrance and/or sac is insufficiently packed, blood flow can persist into the aneurysm.

In some current treatments, an embolic coil is attached to a tubular delivery device and delivered via a delivery catheter to an aneurysm. During delivery, the embolic coil can be engaged to the delivery member's implant detachment/deployment system (referred to herein equivalently as an "detachment system" or "deployment system"). When the embolic coil is in position, the deployment system can release the coil, the coil can be left implanted, and the delivery member can be retracted. Some treatments utilize a mechanical detachment/deployment system that can be actuated by a physician to release the implant by pulling one or more wires or other elongated members referred to generically herein as a "pull wire." Some of the challenges that have been associated with delivering and deploying embolic coils with delivery members having mechanical detachment systems include premature release of a coil due to premature movement of the pull wire proximally, thereby releasing the coil before the system is at the treatment site. This is exacerbated because of the system moves through tortuous vasculature to the treatment site.

There is therefore a need for improved methods, devices, and systems to facilitate implantation of embolic coils and other implants facing similar challenges.

SUMMARY

It is an object of the present invention to provide systems, devices, and methods to meet the above-stated needs. In some examples presented herein, premature proximal movement or translation of a pull wire can be decreased by providing a loop wire that twists one or more times around the pull wire, thereby providing a greater amount of friction against the pull wire.

A detachment system for delivering an implantable medical device to a target location of a body vessel can include a tubular body comprising a lumen extending therethrough and a compressed distal tube. The detachment system can include a loop wire comprising a first end attachment and a second end attachment affixed to the tubular body. The loop wire can further include a loop opening positioned proximate a distal end of the compressed distal tube. The detachment system can include a pull wire extending through the lumen and through the loop opening. The loop wire can include a twist such that that the loop wire is twisted at least one time around the pull wire to increase friction between the loop wire and the pull wire.

The loop wire can be twisted a single time around the pull wire, while in other examples the loop wire can be twisted a plurality of times around the pull wire. Additional twists can increase the friction/tightness of the junction between the pull wire and the loop wire.

The loop wire can include a friction coating proximate the pull wire to increase the friction between the pull wire and loop wire.

The loop wire and the pull wire can be movable to release the implantable medical device from the detachment system.

The twist can inhibit premature detachment of the implantable medical device by inhibiting proximal translation of the pull wire due to frictional resistance provided by the loop wire via the twist.

The tubular body can include a flexible coil disposed in a proximal direction from the compressed distal tube. The loop wire can inhibit elongation of the flexible coil when looped over the pull wire.

The detachment system can include a key affixed to the implantable medical device proximate a proximal end of the implantable medical device. The detachment system can include a stretch resistant fiber engaged to the key, extended through an implant lumen of the implantable medical device, and affixed to the implantable medical device proximate a distal end of the implantable medical device. The key can include a distal opening therethrough, wherein the stretch resistant fiber passes through the distal opening. The key can include a proximal opening therethrough. The key can include a bridge separating the distal opening and the proximal opening. The bridge can support a portion of the pull wire in a distal direction from the loop opening. The twist can be positioned on the loop wire proximal to the bridge.

The pull wire can be weaved across the bridge such that the pull wire passes from a first side of the key, through the proximal opening to a second side of the key and across the bridge, and through the distal opening to the first side of the key.

A detachment system for delivering an implantable medical device to a target location of a body vessel can include a pull wire extending through a tubular body of the detachment system. The detachment system can include a loop wire looped over the pull wire at a distal end of the loop wire and twisted at least once around the pull wire. A twist in the loop wire can inhibit premature detachment of the implantable medical device by inhibiting proximal translation of the pull wire relative to a loop opening in the distal end of the loop wire.

The loop wire can be twisted a single time around the pull wire, while in other examples the loop wire can be twisted a plurality of times around the pull wire. Additional twists can increase the friction/tightness of the junction between the pull wire and the loop wire.

The detachment system can include a compressed distal tube. The tubular body can include a flexible coil disposed in a proximal direction from the compressed distal tube. The loop wire can inhibit elongation of the flexible coil when looped over the pull wire.

The detachment system can include a key affixed to the implantable medical device proximate a proximal end of the implantable medical device. The detachment system can include a stretch resistant fiber engaged to the key, extended through an implant lumen of the implantable medical device, and affixed to the implantable medical device proximate a distal end of the implantable medical device. The key can include a distal opening therethrough, wherein the stretch resistant fiber can pass through the distal opening. The key can include a proximal opening therethrough. The key can include a bridge separating the distal opening and the proximal opening. The bridge can support a portion of the pull wire in a distal direction from the loop opening. The twist can be positioned on the loop wire proximal to the bridge.

A method for constructing a detachment system with an embolic implant and deploying the implant can include providing a tubular body comprising a lumen extending therethrough and a compressible distal tube. The method can include affixing a loop wire to the tubular body. The method can include compressing the compressible distal tube. The method can include positioning a loop opening in the loop wire proximate a distal end of the compressible distal tube such that the loop wire is extended through the lumen. The method can include extending a pull wire through the lumen. The method can include extending the loop opening through a key of an implantable medical device. The method can include twisting the loop wire around the pull wire at least one time. The method can include extending a distal end of the pull wire through the loop opening of the twisted loop wire.

The method to deploy the implant can include inhibiting, via frictional resistance of the twisted loop wire around the pull wire, translation of the pull wire through the loop wire while the implantable medical device is delivered through vasculature to a treatment site. The method can include overcoming frictional resistance such that the pull wire translates proximally and releases the implantable medical device at the treatment site.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive systems and devices, by way of example only, not by way of limitation.

DETAILED DESCRIPTION

An object of the present invention is to decrease the occurrence of or ultimately prevent premature detachment of an embolic coil from a detachment system prior to placing the coil at a treatment site, i.e., an aneurysm. More specifically, it is an object of the present invention to provide additional support to the junction between a loop wire and a pull wire of the detachment system. Certain current designs for embolic coil delivery systems can include a tubular body having a compressed distal tube that, once released from compression, delivers the embolic coil to a treatment site. Within that distal tube (also referred to herein as a "distal hypotube") runs both a loop wire and a pull wire. The loop wire can extend into a detachment features (also referred to herein as a "key") of the implant and loop onto the pull wire to secure the distal hypotube into its compressed state, while also containing the embolic coil that is attached to the key. One common pitfall to prior designs is that there is a chance that the pull wire can prematurely translate proximally from the loop wire, for example, as a physician is delivering the device through tortuosity and reactive frictional forces cause the pull wire to retract. Premature detachment of the detachment system from the embolic coil can be a significant problem, as the physician no longer controls the timing of the detachment of the embolic coil into the aneurysm. The present devices, systems, and methods provide a solution to early, inadvertent deployment of the embolic coil.

Figures 1A, 1B, 1C:
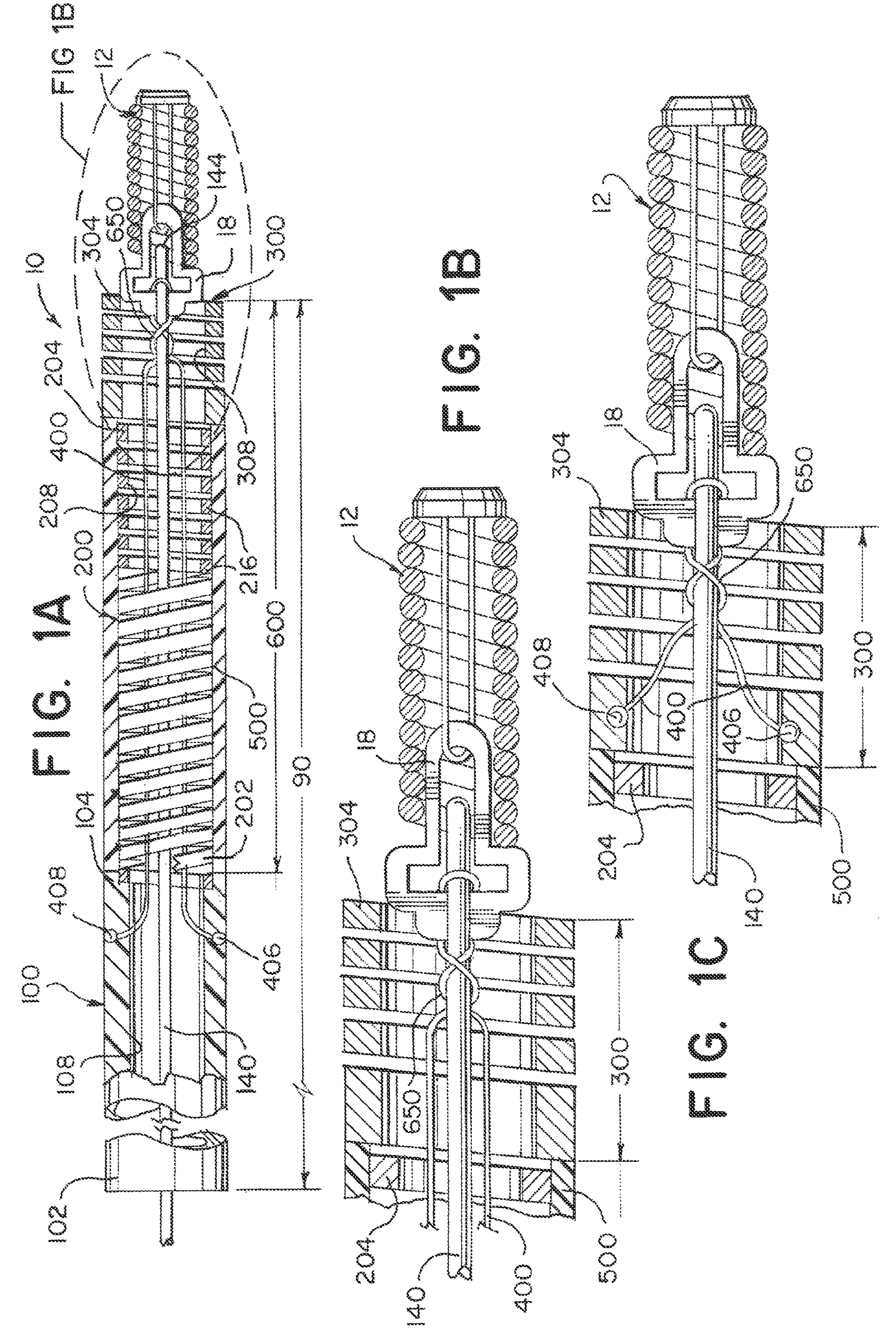
FIG. 1A is an illustration of a delivery/detachment system and implant, according to aspects of the present invention.
FIG. 1B is a detailed view of a detachment system showing a twist in the loop wire proximate the detachment feature (i.e., key), according to aspects of the present invention.
FIG. 1C is another view of a detachment system wherein the loop wire is anchored/attached to the system at a distal tube, according to aspects of the present invention.

Referring to the figures, FIG. 1A is an illustration of a delivery/detachment system 10 and an implantable medical device 12 (which is an embolic coil in the example shown), according to aspects of the present invention. The implantable medical device 12 is also referred to herein as implant 12. The detachment system 10 can include a proximal tube 100, a coiled section 600 comprising a support coil 200, a distal tube 300, a sleeve 500 surrounding the coiled section 600, a loop wire 400 extending through the coiled section 600, and a pull wire 140 extending through the coiled section 600. A distal end 144 of the pull wire 140 can extend at least partially beyond a proximal portion of a key 18 (also referred to herein as "detachment feature") of the implant 12. The detachment system 10 can have a tubular body 90 that is formed by the proximal tube 100, the coiled section 600 comprising the support coil 200, and the distal tube 300. When the distal tube 300 is compressed, as will be described below for when the distal hypotube 300 includes a compressible portion 306, the distal tube 300 can be referred to as a compressed distal tube.

A proximal end 102 of the proximal tube 100 can extend proximally within a delivery member (e.g., catheter 250). A distal end 104 of the proximal tube 100 can be connected to a proximal end 202 of the support coil 200. A distal end 204 of the support coil 200 can be connected to the distal tube 300 at one end, and the implant 12 can be connected to the distal tube 300 at the distal end 304 of the distal tube 300. The proximal tube 100 can include a proximal lumen 108, the coiled section 600 and support coil 200 can include a coil lumen 208, and the distal tube 300 can include a distal lumen 308. The proximal lumen 108, coil lumen 208, and distal lumen 308 provide a contiguous lumen through which the pull wire 140 and loop wire 400 pass.

The coiled section 600 can be formed primarily of a non-radiopaque material, such as steel, and can include a radiopaque section 216 made of a radiopaque material, such as platinum and/or tungsten. The radiopaque section 216 can be positioned between a proximal, non-radiopaque section of the support coil 200 and a distal, non-radiopaque section of the support coil 200. The radiopaque section 216 can be positioned a predetermined distance from a distal end 304 of the detachment system 10 so that a physician can readily visualize the placement of the distal portion of the system during a treatment procedure. The proximal section, radiopaque section 216, and distal section of the support coil 200 can be concentrically welded.

The sleeve 500 can cover at least a portion of the flexible section 106 to inhibit deformation of the flexible section and/or reduce friction with vasculature and the flexible section 106 during intravascular navigation. In some examples, the sleeve 500 can cover about 10 cm of the proximal tube 100 approximate and/or including the distal end 104 of the proximal tube 100. When the detachment system 10 is assembled, the coiled section 600 and sleeve 500 can be more flexible than the distal hypotube 300 and the proximal hypotube 100. One way to measure flexibility is to perform a three-point bend test wherein a portion of the detachment system 10 is held fixed at two end points, a force is applied perpendicularly to the detachment system 10 centrally between the points, and flexibility is quantified by the length of deflection of the detachment system 10 caused by the force. When measured this way, in some examples, the coiled section 600 and sleeve 500 can be about 1.5 times more flexible than the distal hypotube 300 and about 20 times more flexible than the proximal hypotube 100. In other words, when the three-point test is performed identically on the three sections 100, 600, 300, the coiled section 600 can deflect over a length that is about 1.5 time the deflection length of the distal hypotube 300 and about 20 times the length of deflection of the proximal hypotube 100. Flexibility can be measured in other ways as would be appreciated and understood by a person of ordinary skill in the art. When the detachment system 10 is assembled, the coiled section 600 and sleeve 500 can be more flexible than the distal hypotube and the proximal hypotube as flexibility is determined by other means as would be known to a person of ordinary skill in the art.

The loop wire 400 can be attached to the detachment system 10 at locations along the tubular body 90. The loop wire 400 can include a first end attachment 406 to connect the loop wire 400 to the wall of the lumen 108, 208, 308 and a second end attachment 408 to connect an opposite end of the loop wire 400 to the wall of the lumen 108, 208, 308. The first end attachment 406 and second end attachment 408 can be welds, adhesives, or other mechanical fasteners that connect the loop wire 400 to the tubular body 90. The first end attachment 406 and second end attachment 408 can be located along the proximal hypotube 100, as shown in FIG. 1A, or any other location of the tubular body 90, including along the coiled section 600 or the proximal hypotube 300.

The loop wire 400 can include a twist 650 to provide additional resistance/friction between the loop wire 400 the pull wire 140, as described above and shown in FIG. 1A. FIG. 1B provides a detailed view of a detachment system 10 showing the twist 650 in the loop wire 400 proximate a detachment feature (i.e., key 18), according to aspects of the present invention. In prior system, the loop wire 400 is at one side of the pull wire 140 proximal to the key 18. After passing a proximal end of the key 18, the loop wire 400 loops around the key 18 and around the pull wire 140 to the other side of the loop wire 140, thereby securing the key 18 to the pull wire 140. The key 18 (and implant 12) can be deployed from the detachment system 10 by translating the pull wire 140 proximally, beyond the loop in the loop wire 400. In FIG. 1B, the first end attachment 406 and second end attachment 408 are located proximal on the device along tubular body 90. FIG. 1C provides an example of a loop wire 400 that is anchored/attached to the tubular body 90 along the distal tube 300. For example, the first end attachment 406 and second end attachment 408 are positioned along the distal tube 300, which is in accordance with some embodiments.

As described above, one common concern with prior systems is inadvertent proximal translation of the pull wire as the system is deliver through the tortuosity. By twisting the loop wire 400 around the pull wire 140 one or more times, additional resistance prevents inadvertent proximal translation of the pull wire. Additional details and variations of the twist 650 are provided in the discussion of FIGS. 5A-5C. The distal tube 300 can be compressed or a portion of the distal tube 300 can be compressed such that, once the pull wire 140 is removed from the loop at the end of the loop wire 400, the compressed portion of the distal tube 300 can expand to deliver the implant 12. FIGS. 6A-6B provide a detailed view of a compressible portion 306 of the distal hypotube 300.

Figure 2A:
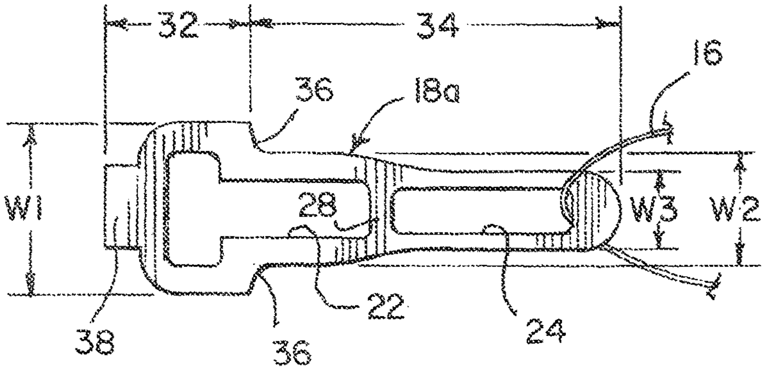
FIGS. 2A and 2B are illustrations of detachment features (i.e., keys) each having a stretch resistant fiber therethrough, according to aspects of the present invention.
Figure 2B:
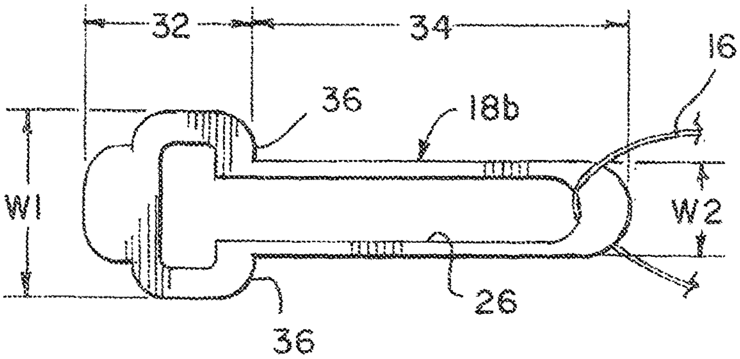

FIGS. 2A and 2B are illustrations of detachment features (i.e., keys 18) each having a stretch resistant fiber 16 therethrough, according to aspects of the present invention. FIG. 2A illustrates a dual opening key 18*a* having a proximal portion 32 that is sized to engage a mechanical detachment system 10 and/or delivery tube (e.g., the distal hypotube 300). The proximal portion 32 is illustrated as having a width W1. The dual opening key 18*a* can have a distal portion 34 that is sized to fit within a lumen 13 of the embolic coil (e.g., implant 12). The distal portion 34 can have a wider section having a width W2 that is about as wide as the inner diameter of the implant 12 and a tapered section having a width W3 that is narrower than the inner diameter of the implant 12. The dual opening key 18*a* can have a proximal tab 38 that is narrower than the proximal portion 32 and is sized to fit within a lumen of a delivery tube (e.g., distal lumen 308). The "dual opening" of the dual opening key 18*a* can refer to the two separate openings within the face of the key 18*a*, for example a proximal opening 22 and a distal opening 24. A bridge 28 can separate the proximal opening 22 and the distal opening 24, as illustrated. The bridge 28 can be used to support the distal end 144 of the pull wire 140 when the detachment system 10 is in the loaded/pre-deployed state.

FIG. 2B illustrates a single opening key 18*b* having a proximal portion 32 that is sized to engage a mechanical detachment system 10 and/or delivery tube (e.g., the distal hypotube 300). The proximal portion 32 is illustrated having a width W1. The single opening key 18*b* can have a distal portion 34 narrower than the proximal portion 32 and sized to fit within the lumen 13 of the implant 12. The single opening key 18*b* can have a proximal tab 38 that is narrower than the proximal portion 32 and sized to fit within a lumen of a delivery tube, as also shown for the dual opening key 18*a*.

When reference is made herein to a key 18, it will be understood to include a dual opening key 18*a* or a single opening key 18*b*. After the key 18 is formed, a stretch resistant fiber 16 can be threaded through a distal opening 24 of the dual opening key 18*a* or the single opening 26 of the single opening key 18*b*. The stretch resistant fiber, which can be a suture material and the like, can secure the key to the embolic coil portion of the implant. The key 18 can include engagement surfaces 36 at a distal end of the proximal portion 32 of the key 18. This engagement surfaces 36 can abut a proximal end 15 of the implant 12.

Figure 3A:
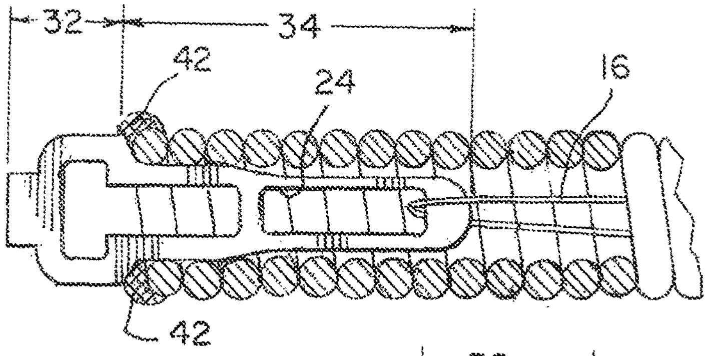
FIGS. 3A-3C are illustrations of detachment features affixed to an embolic coil, according to aspects of the present invention.
Figure 3B:
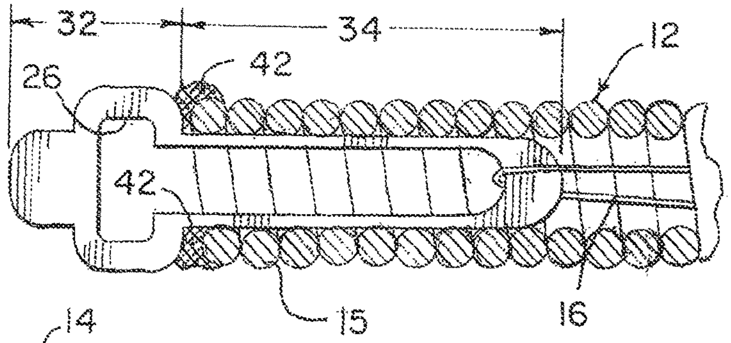
Figure 3C:
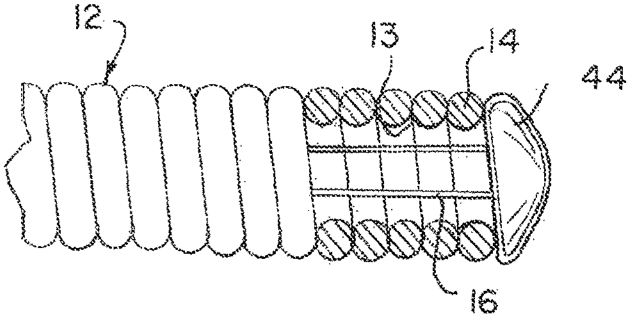

FIGS. 3A-3C are illustrations of keys 18 affixed to an embolic coil (e.g., implant 12), according to aspects of the present invention. In particular, FIGS. 3A and 3B are illustrations of the keys 18 with the distal portion 34 fully inserted into the lumen 13 of the implant 12 and wherein the key 18 is affixed to the implant 12 with welds 42 or other attachments. The welds 52 can be positioned at locations wherein the engagement surfaces 36 of the key 18 meets the proximal end 15 of the implant 12. In both FIGS. 3A and 3B, the key 18 is illustrated having a distal portion 34 that has a width over at least a portion of the length of the distal portion 34 that is about equal to the inner diameter of the lumen 13 of the implant 12.

Figure 4:
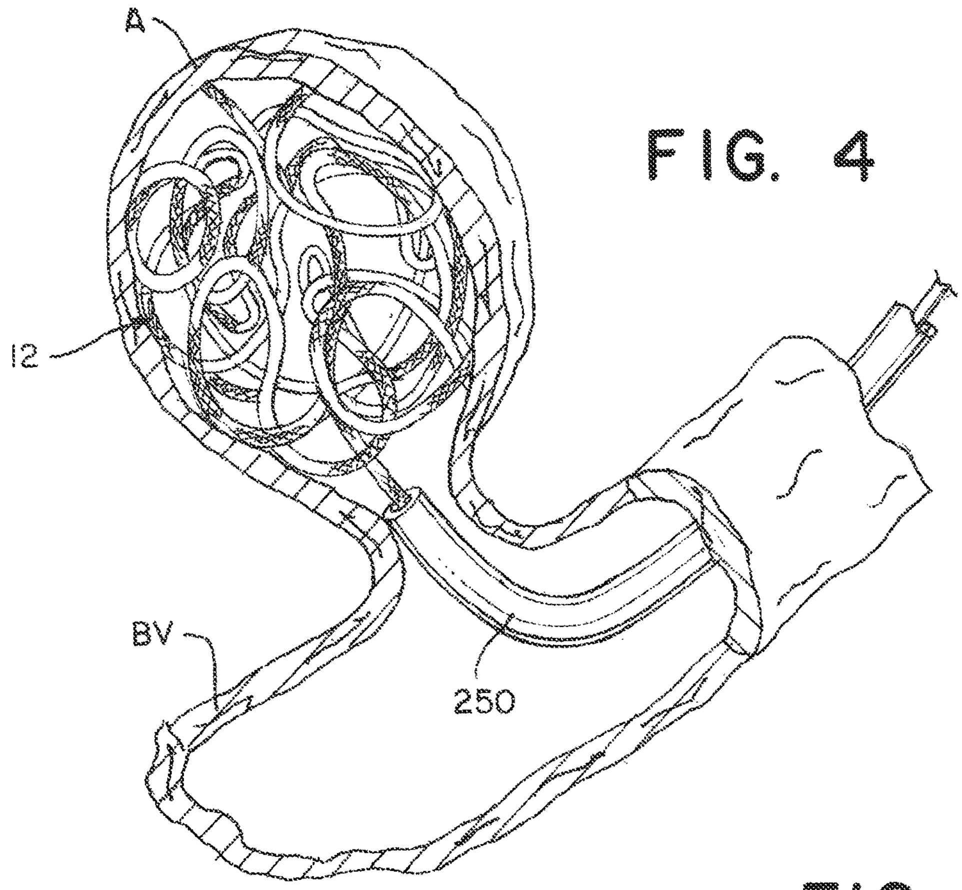
FIG. 4 is an illustration of embolic coils being positioned within an aneurysm, according to aspects of the present invention.

FIG. 4 is an illustration of embolic coils (e.g., implant 12) being positioned within an aneurysm A, according to aspects of the present invention. The detachment system 10 is passed through a blood vessels B V to the aneurysm A through a catheter 250. Once positioned, the implant(s) 12 can loop and bend within the aneurysm sac to form a thrombotic mass. The implant(s) 12 can loop back on themselves and/or loop next to other implants. As the aneurysm A becomes increasingly packed, overlapping portions of the implant 12 can press into each other.

Figure 5A:
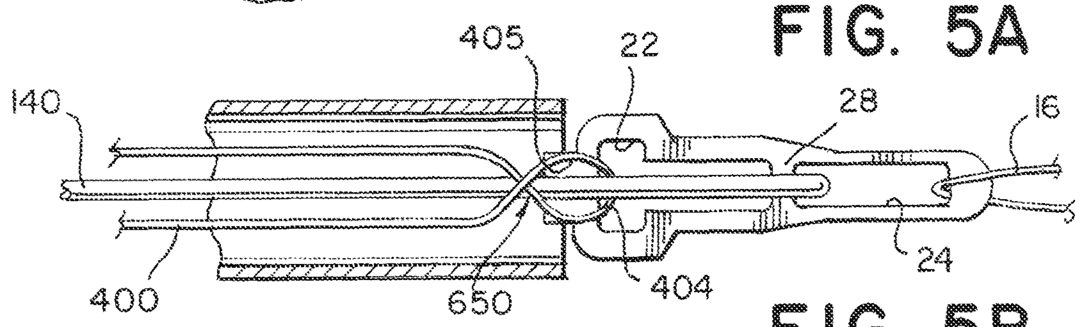
FIGS. 5A-5C are illustrations of example loop wire variations that increase friction at a pull wire, according to aspects of the present invention.
Figure 5B:
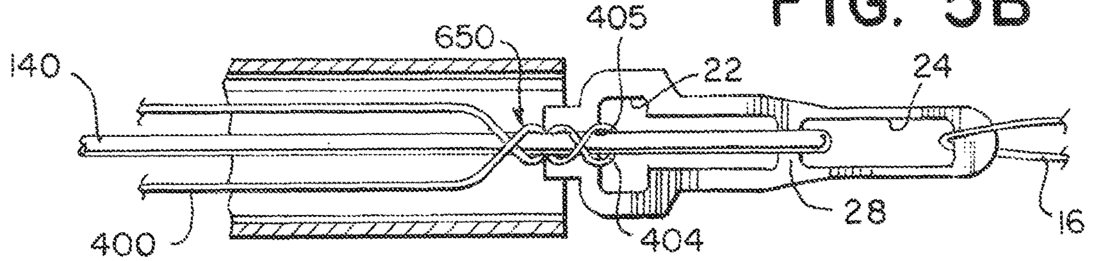
Figure 5C:
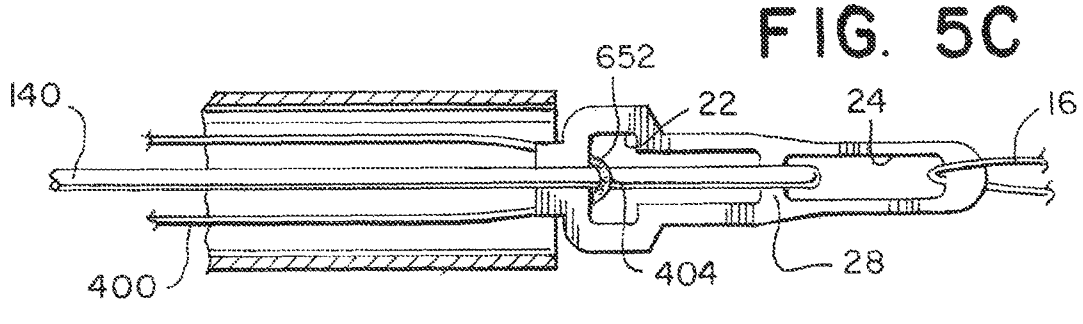
Figure 6A:
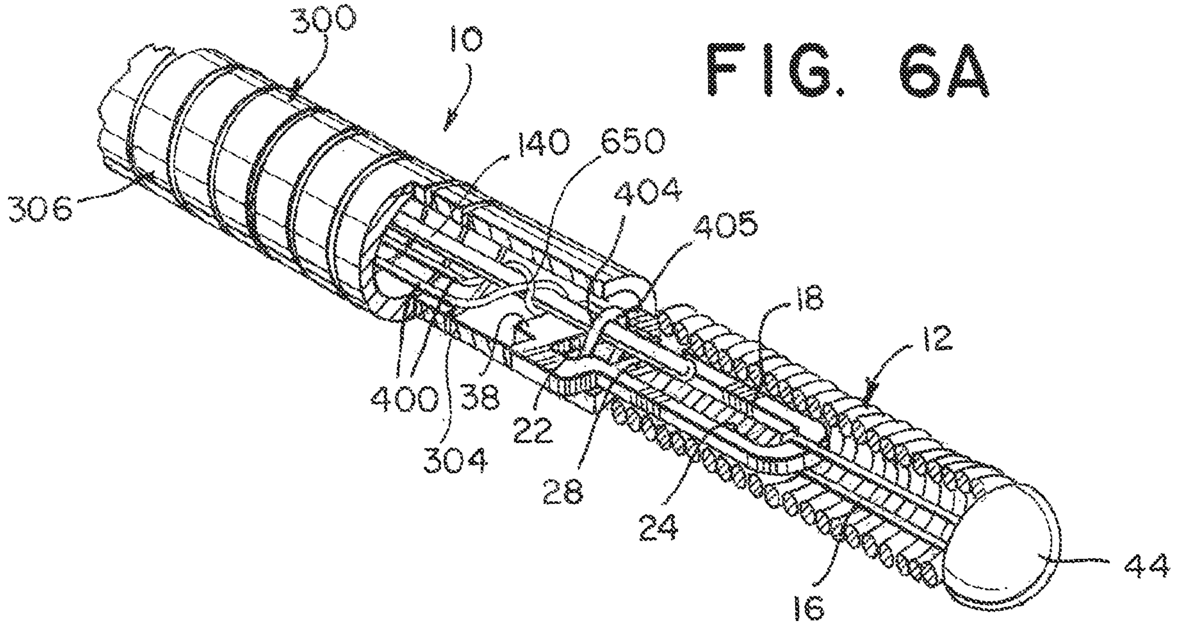
FIGS. 6A-6D illustrate a sequence of steps for releasing an embolic implant from a detachment system, according to aspects of the present invention.
Figure 6B:
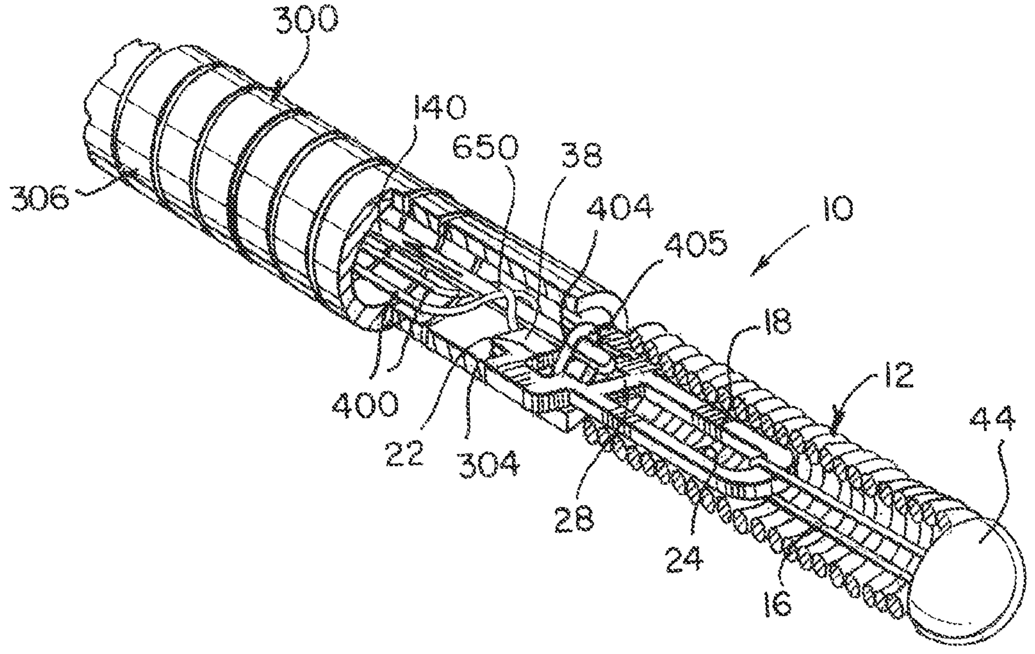

FIGS. 5A-5C are illustrations of example loop wire 400 variations that increase friction at a pull wire 140, according to aspects of the present invention. FIGS. 5A and 5B specifically show variations of twist 650 of the loop wire 400 at a distal end 144 of the pull wire 140. As stated above, the loop wire 400 can extend through the lumen (e.g., lumen 108, 208, 308) of the tubular member on one side of the pull wire 140. After the loop wire passes the proximal end of the key 18 (e.g., the proximal extension 38), the loop wire 400 can cross over the pull wire 140 such and a distal end 404 of the loop wire 400 forms an opening 405 through which the pull wire 140 passes.

The present detachment system 10 can include a twist 650 in the loop wire proximal to where the loop wire 400 crosses over the pull wire 400. The twist 650 causes the loop wire 400 to pass around the pull wire at least one time before terminating at the final, distal opening 405 of the pull wire 400. This twist 650 can be a singular twist, as shown in FIG. 5A, or the twist 650 can be a plurality of twists, as shown in FIG. 5B. The one or more twists 650 can increase the degree of tightness at the distal end 144 of the pull wire 140, thereby preventing unwanted proximal translation and resultant premature deployment of the implant 12. As described above, when the key is a dual opening key 18*a*, the distal end 144 of the pull wire 140 can be supported by the bridge 28 between the proximal opening 22 and the distal opening 24. The twist 650, in these examples, can be positioned proximal to the bridge 28, and the opening 405 in the loop wire 400 can be positioned within the proximal opening 22. When the key is a single opening key 18*b*, the opening 405 of the loop wire 400 can be within the singular opening 26.

Referring to FIG. 5C, example detachment systems 10 can include a friction coating 652 on the distal end 404 of the loop wire 400 proximate the opening 405 in the loop wire 400 through which the pull wire 140 extends. The friction coating 652 can include a silicone, rubber, synthetic polymer, or other coating to increase friction at the junction between the pull wire 140 and the loop wire 400. Alternatively, the distal end 404 of the loop wire 400 can have a roughened surface, for example by providing hatch marks and the like so as to increase the friction at the junction between the pull wire 140 and the loop wire 400. In some examples, the distal end 144 of the pull wire 140 can also be configured to create additional friction. In certain prior system designs, a low-friction polytetrafluoroethylene (PTFE) coating may be applied to the pull wire 140 to decrease friction to enable easier deployment of the implant 12. However, easy deployment can, in some cases, cause inadvertent deployment of the implant. It is contemplated that the distal end 144 of the pull wire 140 does not include a PTFE coating. In some examples, the distal end 144 of the pull wire 140 can include a silicone, rubber, synthetic polymer, or other coating to increase friction at the junction between the pull wire 140 and the loop wire 400. Alternatively, the distal end 144 of the pull wire 140 can have a roughened surface, for example by providing hatch marks and the like so as to increase the friction at the junction between the pull wire 140 and the loop wire 400.

Figure 6C:
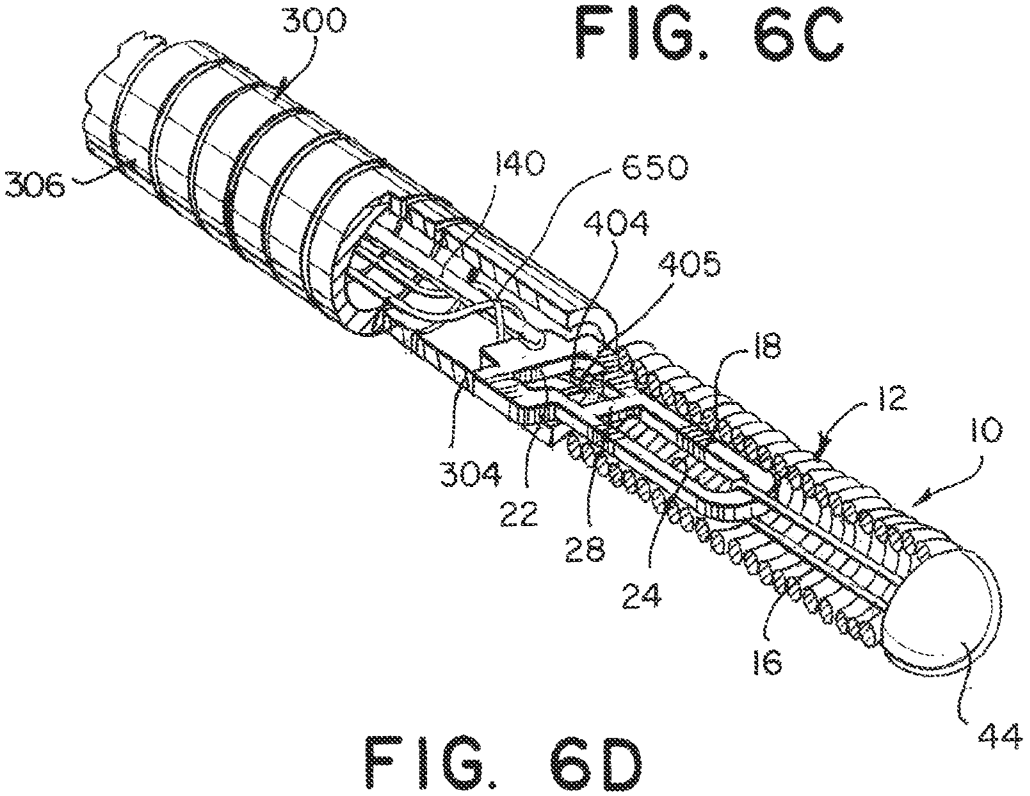
Figure 6D:
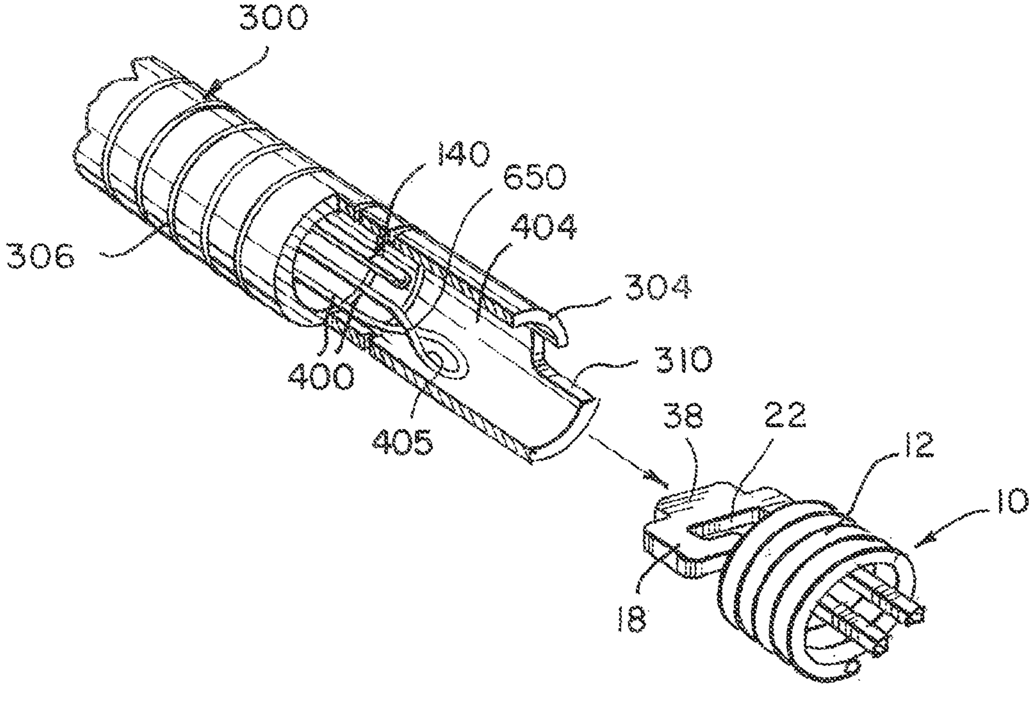

FIGS. 6A-6D illustrate a sequence of steps for releasing an embolic implant 12 from a detachment system 10, according to aspects of the present invention. FIG. 6A is an illustration of the implant 12 and delivery tube (e.g., distal hypotube 300) configured for delivery and positioning of the implant 12. FIGS. 6B through 6D illustrate releasing the example embolic implant 12 from the distal hypotube 300. A portion of the distal hypotube 300 is cut away for illustration purposes. The more proximal features of the tubular body 90 are not shown in the views.

FIG. 6A illustrates the detachment system including a pull wire 140 and a loop wire 400 locked into the key 18 of the implant 12 (the key shown in FIGS. 6A-6D is a dual opening key 18*a*, but the illustrations could equally apply to a single opening key 18*b* or a triple opening key 18*c*). The distal tube 300 can include a compressible portion 306. The loop wire 400 can have an opening 405 at a distal end 404 of the loop wire 400, and the opening 405 can be placed through an opening in the key 18 (e.g., proximal opening 22 in a dual opening key 18*a*, or the singular opening 26 in a single opening key 18*b*). As described above, the twist 650 can be twisted around the pull wire 140 proximal to the terminating end, i.e., the opening 405 through which the pull wire 140 extends. When the pull wire 140 is placed through the opening 405, the implant 12 is now secure.

In the case of a dual opening key 18*a*, the key can include a bridge 28 positioned distally from the loop wire opening 405 and positioned to support a distal portion of the pull wire 140 that is distal of where the loop wire opening 405 wraps around by the pull wire 140. Configured thusly, the bridge 28 can support the distal portion of the pull wire 140 such that when the loop wire 400 tensions against the pull wire 140 at the loop opening 405, the bridge 28 can inhibit the distal portion of the pull wire 140 from deforming. The proximal tab 38 of the key 18 can be positioned to support a portion of the pull wire 140 that is proximal of where the loop wire opening 405 is supported by the pull wire 140. The combination of the bridge 28 and the proximal tab 38 can inhibit the pull wire 140 from deforming due to forces applied by the loop wire 400. The distal hypotube 300 can be detachably attached to the implant 12 as illustrated in FIG. 6A during delivery of the implant 12 through the vasculature and while the implant 12 is being positioned at a treatment site. The bridge 28 can reduce the likelihood that the implant 12 is prematurely released due to bending of the pull wire 140 due to forces from the loop wire 400.

FIG. 6B illustrates the pull wire 140 being drawn proximally to begin the release sequence for the implant 12. FIG. 6C illustrates the instant the pull wire 140 exits the opening 405 and is pulled free of the loop wire 400. The distal end 404 of the loop wire 400 falls away and exits the key 18. As can be seen, there is now nothing holding the implant 12 to the distal hypotube 300. FIG. 6D illustrates the end of the release sequence. Here, the compressible portion 306 has expanded/returned to its original shape and "sprung" forward. An elastic force E is imparted by the distal end 304 of the distal hypotube 300 to the implant 12 to "push" it away to ensure a clean separation and delivery of the implant 12. The compressible portion 306 can be a spiral cut portion of the distal hypotube 300, for example a laser cut spiraled segment that can be compressed when the detachment system 10 is loaded.

Figure 7:
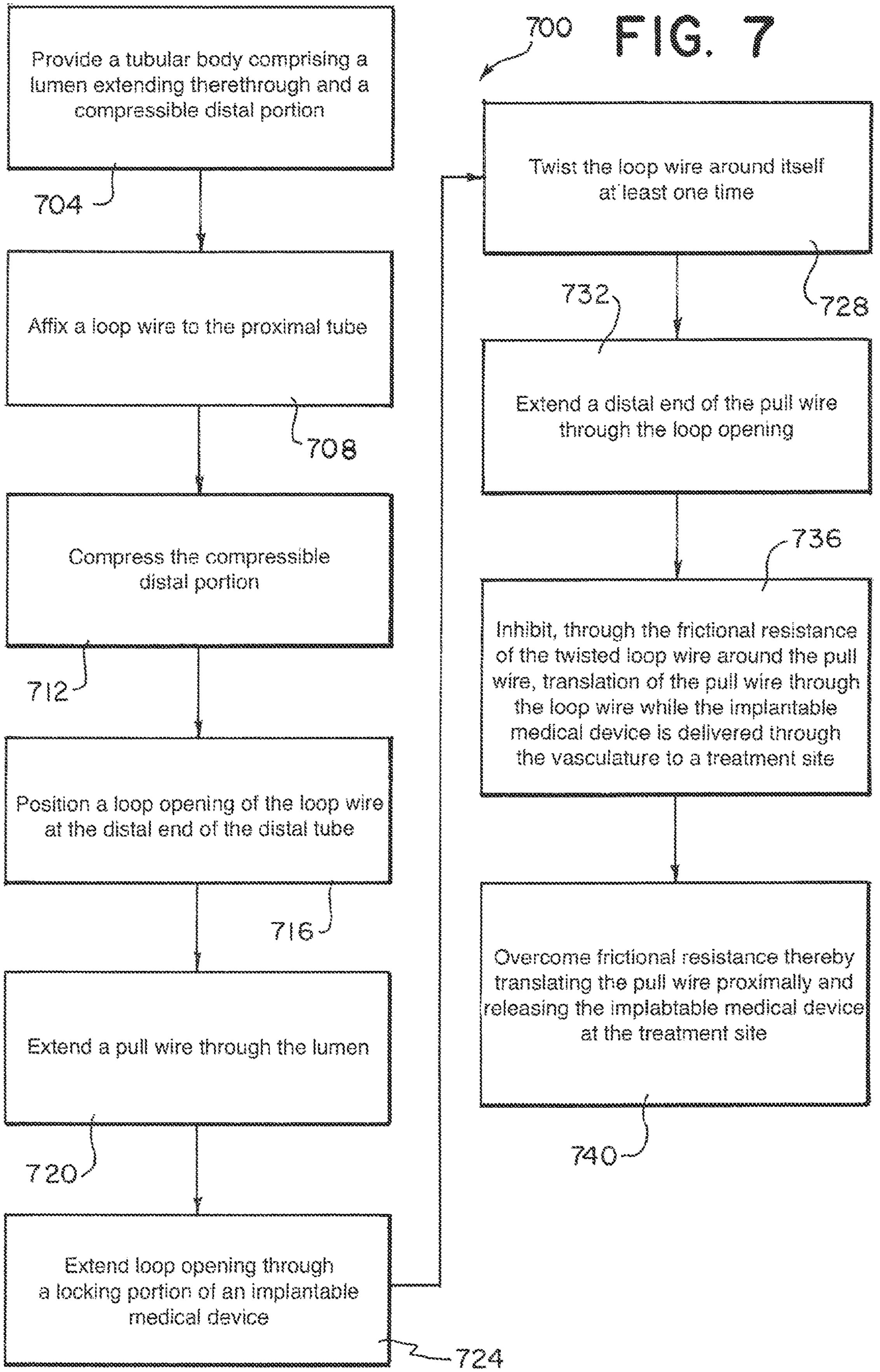
FIG. 7 is a flow diagram illustrating steps for designing, constructing, or configuring a detachment system and implant, according to aspects of the present invention.

FIG. 7 is a flow diagram illustrating a method 800 for designing, constructing, or configuring a detachment system 10 and implant 12, according to aspects of the present invention. Steps 704 through 732 describe steps to create/construct one or more of detachment systems 10 described herein. In step 704, the construction of the detachment system 10 can begin with providing a tubular body 90 comprising a lumen (e.g., lumen 108, 208, 308) extending therethrough and a compressible distal tube (e.g., distal hypotube 300). In step 708, a loop wire 400 can be affixed to the tubular body 90. For example, proximal ends of the loop wire can be attached to the tubular body at a first end attachment 406 and a second end attachment 408.

In step 712, the compressible distal tube 300 can be compressed into its loaded configuration. At step 716, a loop wire opening 405 in the loop wire 400 can be positioned proximate a distal end 304 of the compressible distal tube such that the loop wire 400 is extended through the lumen (e.g., lumen 108, 208, 308). In step 720, the pull wire 140 can be extended through the lumen (e.g., lumen 108, 208, 308).

In step 724, the loop opening 405 can be extended through a key 18 of an implantable medical device 12. In step 728, the loop wire 400 can be twisted around the pull wire 140 at least one time, thereby creating the loop wire twist 650 described herein. In step 732, a distal end 144 of the pull wire 140 can be extended through the twist 650 and loop opening 405 of the twisted loop wire 140.

The steps for creating/constructing the detachment system 10 can end after step 732. In some examples, steps 736 and 740 provide additional steps to inhibit inadvertent proximal translation of the pull wire 140 and such that the implant can be deployed. For example, in step 736, proximal translation of the pull wire 140 through the loop wire 400 while the implantable medical device 12 is delivered through vasculature to a treatment site can be inhibited via frictional resistance of the twisted loop wire 400 around the pull wire 140. In step 740, frictional resistance of the junction between the loop wire 400 and pull wire 140 can be overcome such that the pull wire 140 translates proximally and releases the implantable medical device 12 at the treatment site.

Figure 8A:
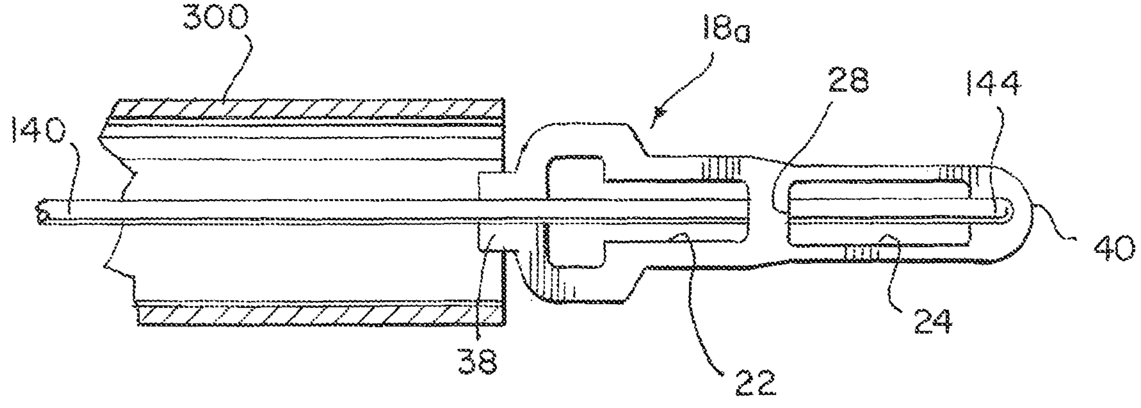
FIG. 8A is an illustration of a design for a detachment feature (i.e., key) that enables the pull wire to weave around a bridge, according to aspects of the present invention.
Figure 8B:
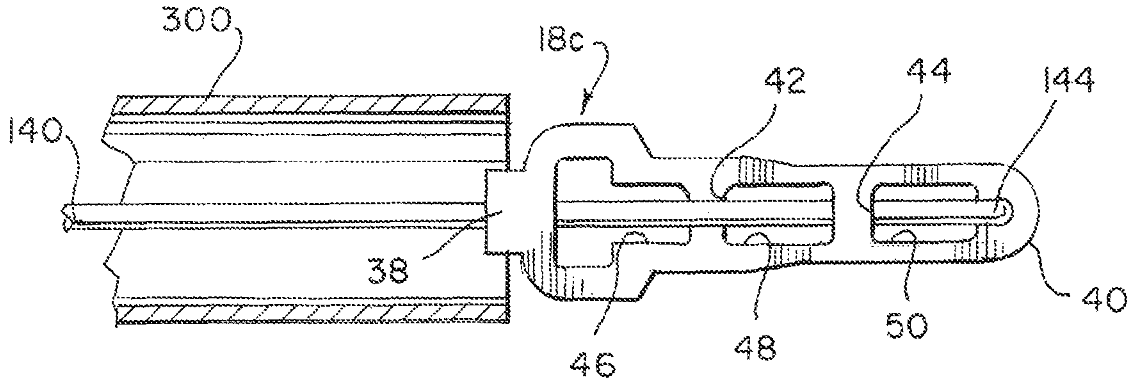
FIG. 8B is an illustration of a design for a detachment feature (i.e., key) that enables the pull wire to weave around multiple bridges, according to aspects of the present invention.

In some examples, the key 18 can be designed to provide additional friction at the pull wire 140 so as to further inhibit premature proximal translation of the pull wire 140. FIGS. 8A and 8B provide examples of such a construct, wherein the pull wire 140 can be weaved around one or more bridges of the key 18. FIG. 8A shows a "dual opening" key 18*a*, as shown and described above with reference to FIG. 2A. The key 18*a* can include a bridge 28 to separate the proximal opening 22 and the distal opening 24, as illustrated. In some examples, the pull wire 140 can be weaved around the bridge 28 to create additional friction at the junction between the pull wire 140 and key 18*a*. For example and as shown in FIG. 8A, the pull wire 140 can pass over the proximal tab 38 of the key 18*a* at a first side of the key 18*a*, pass over/under the bridge 28 on a second side of the key 18*a*, weave back to the first side of the key 18*a*, and rest upon a distal end 40 of the key 18*a* on the first side of the key 18*a*. In weaving the pull wire 140 around the bridge 28, the pull wire 140 can have a stronger engagement with the key 18*a* so as to inhibit inadvertent proximal translation of the pull wire 140.

In some examples, the key 18 can include a plurality of bridges to enable more weaving of the pull wire 140 and thus provide additional friction. Referring to FIG. 8B, the key 18*c* (e.g., a triple-opening key) includes a first bridge 42 and a second bridge 44. The first bridge 42 creates a first opening 46 between the proximal tab 38 and the first bridge 42. The second bridge 44 creates a second opening 48 between the first bridge 42 and the second bridge 44, as well as a third opening 50 between the second bridge 44 and the distal end 40 of the key 18*c*. In this example design, the pull wire 140 can weave around the first bridge 42 and second bridge 44 through the first opening 46, the second opening 48, and the third opening 50. To illustrate, the pull wire 140 can pass over the proximal tab 38 of the key 18*c* at a first side of the key 18*a*, pass over/under the first bridge 42 on a second side of the key 18*c*, pass under/over the second bridge 44 on the first side of the key 18*c*, weave back to the second side of the key 18*c*, and rest upon a distal end 40 of the key 18*c* on the second side of the key 18*c*. It will be understood that the weaved pull wire 140 described with reference to FIGS. 8A and 8B can be used along with the twisting loop wires 400 described herein; it will also be understood that the weaved pull wire 140 described with reference to FIGS. 8A and 8B can be implemented as an alternative to the twisting loop wires 400 as a means to increase friction.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%.

The descriptions contained herein are examples of embodiments of the invention and are not intended in any way to limit the scope of the invention. As described herein, the invention contemplates many variations and modifications of the implant and methods for making and using the same, including alternative materials, alternative geometries of component parts, alternative positioning of component parts in relation to each other, etc. These modifications would be apparent to those having ordinary skill in the art to which this invention relates and are intended to be within the scope of the claims which follow.

What is claimed is:

1. A detachment system for delivering an implantable medical device to a target location of a body vessel, the system comprising:

a tubular body comprising a lumen extending therethrough and a compressed distal tube;

a loop wire comprising a first end attachment and a second end attachment each affixed to the tubular body and further comprising a loop opening positioned proximate a distal end of the compressed distal tube, the loop wire extending through the lumen; and a pull wire extending through the lumen and through the loop opening, wherein the loop wire comprises a twist such that that the loop wire is twisted at least one time around the pull wire to increase friction between the loop wire and the pull wire.

2. The detachment system of claim 1, wherein the loop wire is twisted a plurality of times around the pull wire.

3. The detachment system of claim 1, wherein a distal end of the loop wire comprises a friction coating proximate the pull wire.

4. The detachment system of claim 1, wherein the loop wire and the pull wire are movable to release the implantable medical device from the detachment system.

5. The detachment system of claim 1, wherein the twist is effective to inhibit premature detachment of the implantable medical device by inhibiting proximal translation of the pull wire due to frictional resistance provided by the loop wire via the twist.

6. The detachment system of claim 1, wherein the tubular body further comprises a flexible coil disposed in a proximal direction from the compressed distal tube, wherein the loop wire inhibits elongation of the flexible coil when looped over the pull wire.

7. The detachment system of claim 1, further comprising:

a key affixed to the implantable medical device proximate a proximal end of the implantable medical device; and a stretch resistant fiber engaged to the key, extended through an implant lumen of the implantable medical device, and affixed to the implantable medical device proximate a distal end of the implantable medical device.

8. The detachment system of claim 7, wherein the key comprises:

a distal opening therethrough, wherein the stretch resistant fiber passes through the distal opening;

a proximal opening therethrough; and a bridge separating the distal opening and the proximal opening.

9. The detachment system of claim 8, wherein the bridge supports a portion of the pull wire in a distal direction from the loop opening.

10. The detachment system of claim 9, wherein the twist is positioned in the loop wire proximal to the bridge.

11. The detachment system of claim 8, wherein the pull wire is weaved across the bridge such that the pull wire passes from a first side of the key, through the proximal opening to a second side of the key and across the bridge, and through the distal opening to the first side of the key.

12. A detachment system for delivering an implantable medical device to a target location of a body vessel, the system comprising:

a pull wire extending through a tubular body of the detachment system; and a loop wire looped over the pull wire at a distal end of the loop wire and twisted at least once around the pull wire; and a compressed distal tube, wherein the tubular body comprises a flexible coil disposed in a proximal direction from the compressed distal tube, wherein the loop wire inhibits elongation of the flexible coil when looped over the pull wire, and wherein a twist in the loop wire is effective to inhibit premature detachment of the implantable medical device by inhibiting proximal translation of the pull wire relative to a loop opening in the distal end of the loop wire.

13. The detachment system of claim 12, wherein the loop wire is twisted a plurality of times around the pull wire.

14. The detachment system of claim 12, further comprising:

a key affixed to the implantable medical device proximate a proximal end of the implantable medical device; and a stretch resistant fiber engaged to the key, extended through an implant lumen of the implantable medical device, and affixed to the implantable medical device proximate a distal end of the implantable medical device.

15. The detachment system of claim 14, wherein the key comprises:

a distal opening therethrough, wherein the stretch resistant fiber passes through the distal opening;

a proximal opening therethrough; and a bridge separating the distal opening and the proximal opening.

16. The detachment system of claim 15, wherein the bridge supports a portion of the pull wire in a distal direction from the loop opening.

17. The detachment system of claim 16, wherein the twist is positioned in the loop wire proximal to the bridge.

18. A method comprising:

providing a tubular body comprising a lumen extending therethrough and a compressible distal tube;

affixing a loop wire to the tubular body;

compressing the compressible distal tube;

positioning a loop opening in the loop wire proximate a distal end of the compressible distal tube such that the loop wire is extended through the lumen;

extending a pull wire through the lumen;

extending the loop opening through a key of an implantable medical device;

twisting the loop wire around the pull wire at least one time; and extending a distal end of the pull wire through the loop opening of the twisted loop wire.

19. The method of claim 18, further comprising:

inhibiting, via frictional resistance of the twisted loop wire around the pull wire, translation of the pull wire through the loop wire while the implantable medical device is delivered through vasculature to a treatment site; and overcoming frictional resistance such that the pull wire translates proximally and releases the implantable medical device at the treatment site.

* * * * *